(12) United States Patent
Sioutas

(10) Patent No.: US 6,786,105 B1
(45) Date of Patent: Sep. 7, 2004

(54) PERSONAL PARTICLE MONITOR

(75) Inventor: Constantinos Sioutas, Los Angeles, CA (US)

(73) Assignee: University of Southern California, Los Angeles, CA (US)

(*) Notice: Subject to any disclaimer, the term of this patent is extended or adjusted under 35 U.S.C. 154(b) by 0 days.

(21) Appl. No.: 10/268,399

(22) Filed: Oct. 9, 2002

Related U.S. Application Data

(60) Provisional application No. 60/328,527, filed on Oct. 9, 2001.

(51) Int. Cl.[7] ............................................. G01N 15/02
(52) U.S. Cl. ..................................................... 73/863.22
(58) Field of Search ........................... 73/863.22, 863.23

(56) References Cited

U.S. PATENT DOCUMENTS

| | | | | |
|---|---|---|---|---|
| 4,327,594 A | * | 5/1982 | Nelson ..................... | 73/863.22 |
| 4,387,603 A | * | 6/1983 | Nelson ..................... | 73/863.22 |
| 4,570,494 A | * | 2/1986 | Dunn et al. ............... | 73/863.22 |
| 5,343,767 A | * | 9/1994 | Marple et al. ............ | 73/863.22 |
| 5,425,802 A | | 6/1995 | Burton et al. ............ | 95/32 |
| 5,437,198 A | * | 8/1995 | John ......................... | 73/863.22 |
| 5,571,945 A | | 11/1996 | Koutrakis et al. ........ | 73/28.03 |
| 5,788,741 A | | 8/1998 | Burton et al. ............ | 95/32 |
| 5,854,431 A | * | 12/1998 | Linker et al. ............. | 73/863.23 |
| 5,932,795 A | | 8/1999 | Koutrakis et al. ........ | 73/28.01 |
| 5,985,140 A | * | 11/1999 | Dewaele ................... | 210/198.2 |
| 6,431,014 B1 | | 8/2002 | Liu et al. .................. | 73/863.22 |

OTHER PUBLICATIONS

Misra, et al., "Development and evaluation of a personal cascade impactor sampler (PCIS)", *Journal of Aerosol Science*, vol. 33, pp. 1027–1047, 2002.

* cited by examiner

Primary Examiner—Hezron Williams
Assistant Examiner—Katina Wilson
(74) Attorney, Agent, or Firm—Fish & Richardson P.C.

(57) ABSTRACT

Provided is a personal sampler for PM that allows separation of airborne particles in several size ranges and operates at a high flow rate (9 L/min) by personal sampling standards that makes chemical analysis of the size-fractionated particles possible within a period of 24 hours or less.

25 Claims, 13 Drawing Sheets

Figure 3B:
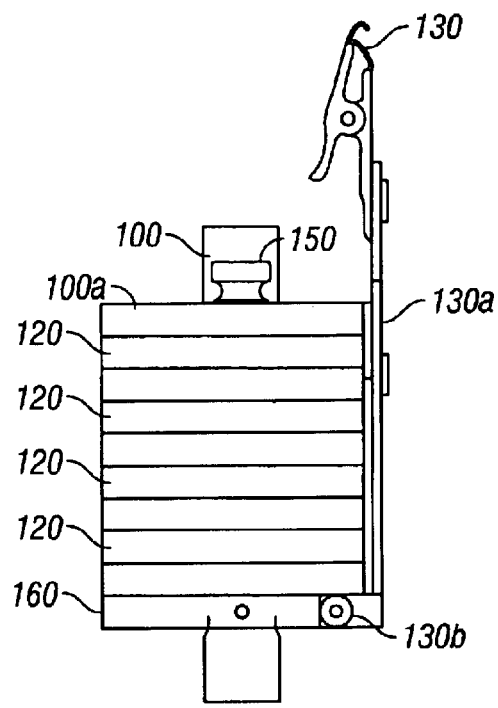

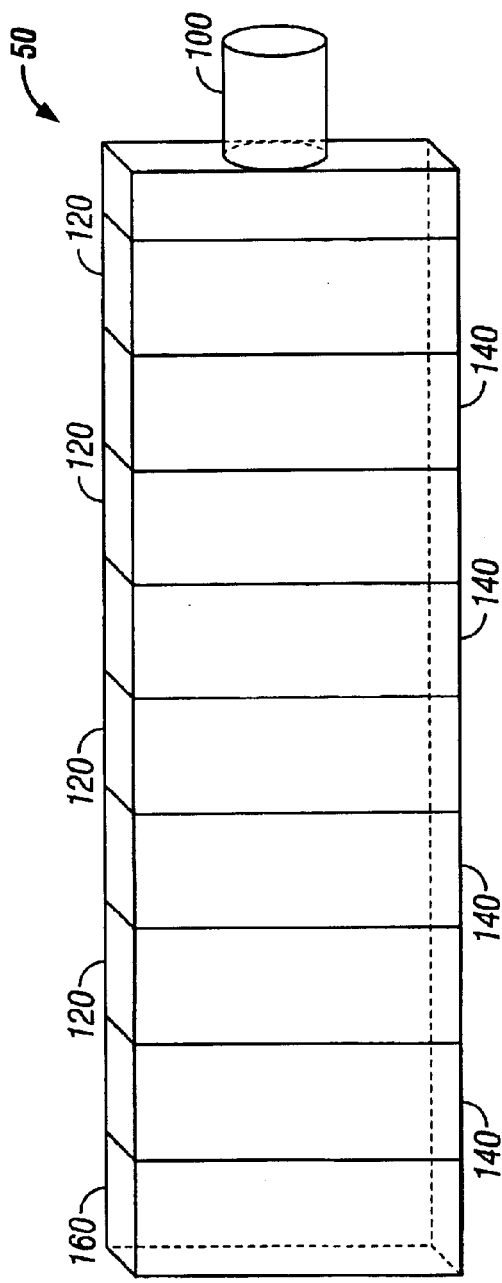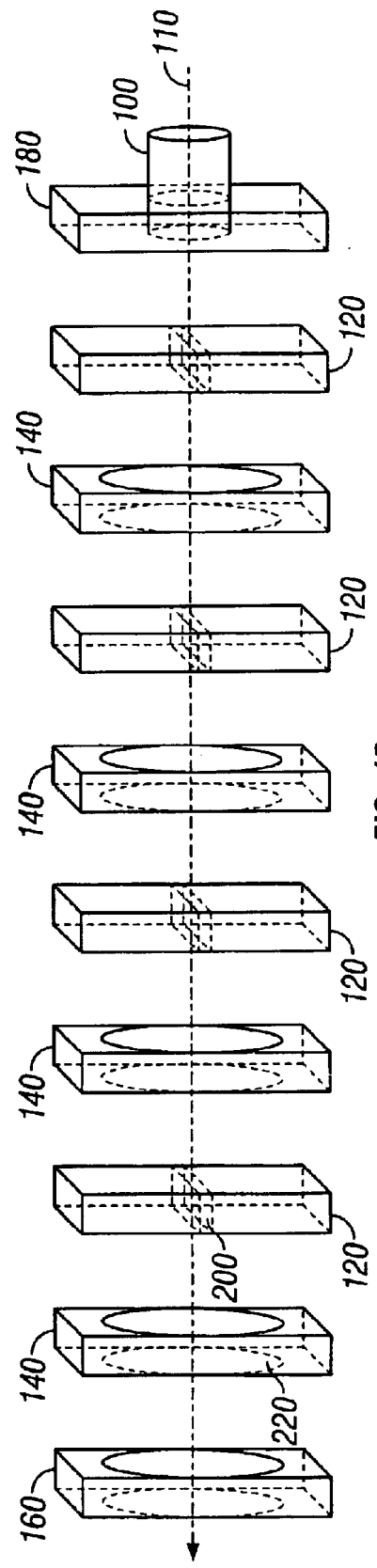
FIG. 1A
FIG. 1B

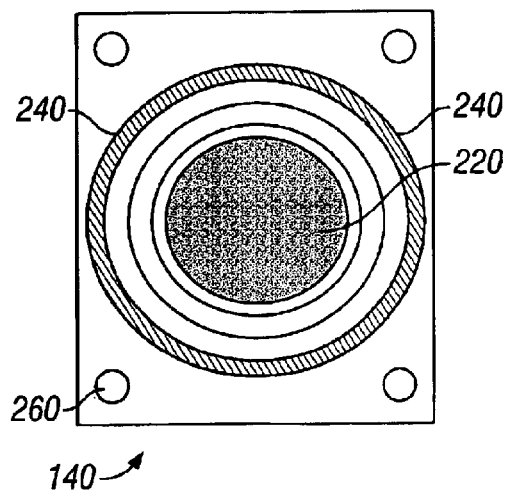
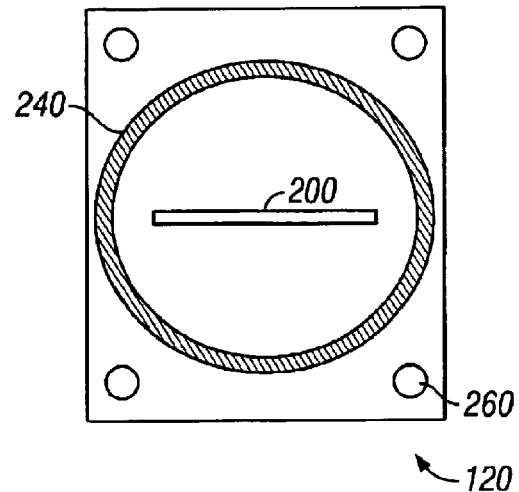
FIG. 2A  FIG. 2B
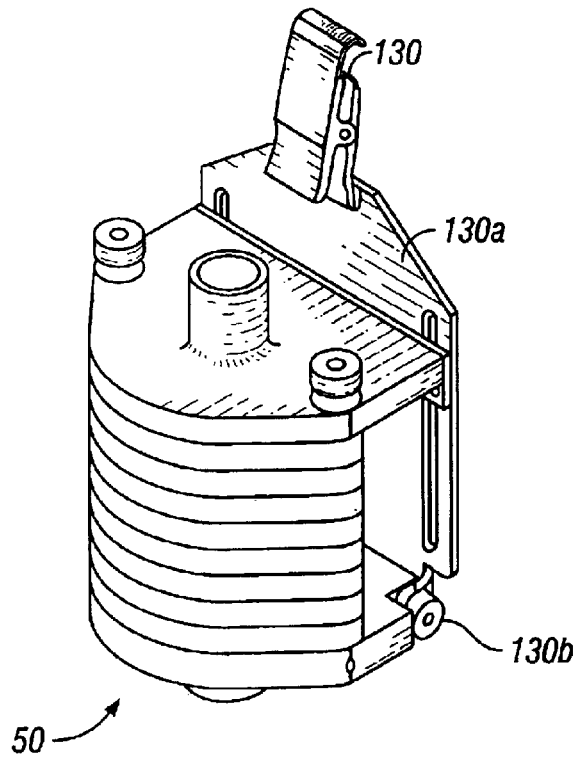
FIG. 3A

PERSONAL PARTICLE MONITOR

CROSS REFERENCE TO RELATED APPLICATIONS

The present application claims priority under 35 U.S.C. §119 to U.S. Provisional Application Serial No. 60/328,527, filed Oct. 9, 2001, the disclosure of which is incorporated herein by reference.

NOTICE OF GOVERNMENT CONTRACT

This invention was made with government support under Contract No. W001013 awarded by the National Center for Environmental Research. The government has certain rights in the invention.

TECHNICAL FIELD

This invention relates to methods for measuring particulate matter in gas, such as for environmental sampling.

BACKGROUND

Epidemiological studies in the U.S.A. and abroad have shown associations between mortality and morbidity and human exposure to ambient particulate matter (Schartz and Dockery, Am. Rev. Resp. Dis. 145:600, 1992; Pope et al., Am. Rev. Resp. Dis. 144:668, 1992). To date, there is limited knowledge about physical or chemical properties of particulate matter that are responsible for these health effects and there is an increasing interest in developing accurate measurements in the near future.

These associations have been initially demonstrated for total suspended particulates (TSP) and particulate matter (PM) with a diameter of <10 $\mu$m ($PM_{10}$); however, results from other studies suggest that fine particles ($PM_{2.5}$) and particle components, such as sulfate ($SO_4^{2-}$), and aerosols with strong acidity ($H^+$), also may be associated with increased mortality and other adverse health impacts (Ayres et al., Environ. Health Persp. 79:83–88, 1989; Bates and Sizto, Environ. Health Persp. 79(1):69–72, 1989; Bates et al., Environ. Res. 51(1):51–70, 1990; Dockery et al., Am. Rev. Resp. Dis. 147(4):A633, 1993; Raizenne et al., Am. Rev. Resp. Dis. 147(4):A635, 1993; Raizenne et al., Environ. Health Persp. 79:179–185, 1989; Thurston et al., J. Expos. Anal. Environ. Epid. 2(4):429–450, 1992; and Thurston et al., Amer. Rev. Resp. Dis. 147(4):A633, 1993).

The U.S. EPA has recently recognized the need to develop continuous measurement techniques for inhalable particulate matter ($PM_{10}$ and $PM_{2.5}$). Results from several studies have begun to expand our knowledge about the relationship between outdoor, indoor, and personal levels of $PM_{10}$ and $PM_{2.5}$, and sub-components thereof such as $SO_4^{2-}$ and $H^+$. Outdoor studies conducted to date (Lioy et al., J. of the Air Poll. Cont. Assoc. 38:668–670, 1988; Suh et al. J. of Expos. Anal. And Environ. Epid. 4:1, 1994; Jones et al., Atmosph. Environ., 2000) have provided convincing evidence that outdoor $PM_{10}$, $PM_{2.5}$, and $SO_4^{2-}$ concentrations are quite uniform within both rural and urban communities. The same studies have also shown that outdoor $H^+$ concentrations do not vary spatially within rural communities, but may exhibit substantial spatial variation within urban environments. From studies of indoor environments, it is clear that significant fractions (50–90%) of outdoor $PM_{10}$, $PM_{2.5}$, $SO_4^{2-}$, and $H^+$ penetrate indoors (Thomas et al., J. Exp. Anal. And Environ. Epid. 3(2):203–226, 1993; Wallace, J. of the Air and Waste Manag. Assoc. 46(2):98–126, 1996; Abt et al., Environ. Sci. and Tech., 2000). Once indoors, these particulate species may be deleted through deposition onto surfaces, or in the case of $H^+$, through reaction with other pollutants present indoors. Indoor particulate concentrations are further affected by the myriad of indoor sources, which include cooking, resuspension, and smoking. As a result of these sources, indoor particulate concentrations are often higher than corresponding outdoor levels. These findings, in conjunction with the fact that people spend the majority of their time indoors, suggest indoor sources to be important contributors to personal exposures to $PM_{10}$ and $PM_{2.5}$.

Several studies have found both indoor and outdoor concentrations to be poor estimators of personal exposures to $PM_{10}$ and its components, as neither indoor nor outdoor concentrations suffice to account for the observed interpersonal variability in their exposures. Daytime personal $PM_{10}$ exposures were found to be approximately 50% higher than corresponding indoor and outdoor levels (Thomas et al., J. Exp. Anal. And Envrion. Epid., 3(2), 203–226, 1993), while personal $SO_4^{2-}$ and $H^+$ exposures were found to be higher than indoor, but lower than outdoor concentrations (Suh et al., supra). The concentration of a pollutant varies from location to location; therefore concentration values obtained by stationary monitors may not be representative of human exposures to particulate pollutants. Furthermore, a person's activities can alter the patterns of exposure to contaminants throughout the day.

In order to accurately assess individual exposures to ambient particles it becomes necessary to use personal monitors. Nevertheless, the development of reliable personal particle monitors has been impeded by several technical challenges. The smaller sampling pump size, the reduced volume or surface of the collection medium and finally the fact that the energy source required for the device is from a self-contained source, all limit the amount that can be collected within a time period (Clayton et al., J. Exp. Anal. And Environ. Epid., 3(2):227–250, 1993; Morandi et al., Environ. Monitor. And Assess. 10(2):105–122, 1988; Spengler et al., Environ. Sci. and Technol. 19:700–707, 1985). In addition, existing personal monitoring devices provide very little information in the PM size distribution (at best they measure PM concentration below 2.5 $\mu$m). Information obtained from more accurate personal monitoring devices that are user-friendly and inexpensive will allow large populations to be studied, thereby providing the much-needed data on the relationship between outdoor and indoor concentrations and personal exposures as a function of particle size and chemical compositions.

SUMMARY

The invention provides a personal sampler for PM that allows separation of airborne particles in several size ranges and operates at a high flow rate (9 L/min) by personal sampling standards that makes chemical analysis of the size-fractionated particles possible within a period of 24 hours or less.

The invention provides a personal cascade impactor sampler (PCIS), comprising a miniaturized cascade impactor. The miniaturized cascade impactor comprises four impactor stages followed by an after-filter. The PCIS operates at a flow rate of about 9 liters per minute and has a pressure drop of about 11 in $H_2O$.

The invention provides a device comprising an inlet port at a first end; a plurality of orifice plates, each orifice plate comprising an orifice; a plurality of impactor stage plates, each impactor stage plate comprising an impaction surface having a predetermined cutpoint for particulate matter; and a filter plate at a second end, wherein the inlet port is fluidly connected to the filter plate such that a pressure drop from the first end to the second end is between about 8 and 15 inches of $H_2O$, each orifice plate and impactor stage plate alternately disposed between the first end and second end, wherein each orifice plate is immediately followed by an impactor stage plate.

The invention further provides a personal cascade impactor sampler (PCIS) system. The PCIS comprises a miniaturized cascade impactor assembly (MCIA) having an inlet port at a first end; a plurality of orifice plates, each orifice plate having an orifice; a plurality of impactor stage plates, each impactor stage plate comprising an impaction surface having a predetermined cutpoint for particulate matter; and a filter plate at a second end, wherein the inlet port is fluidly connected to the filter plate such that a pressure drop from the first end to the second end is between about 8 and 15 inches of $H_2O$, each orifice plate and impactor stage plate alternately disposed between the first end and second end, wherein each orifice plate is immediately followed by an impactor stage plate. The PCIS system also comprises a pump, fluidly connected to the MCIA and a power device such as, for example, a lithium battery pack in electrical communication with the pump.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a depiction of a miniaturized personal cascade impactor assembly.

FIG. 1B depicts the individual stages of a miniaturized cascade impactor assembly.

FIG. 2 is a planar view of an impactor stage and orifice plate.

FIG. 3 is a further depiction of a miniaturized personal cascade impactor assembly.

FIG. 4 shows further detail of an inlet plate of a miniaturized personal cascade impactor assembly.

FIG. 5 shows further detail of an orifice plate of a miniaturized personal cascade impactor assembly.

FIG. 6 shows further detail of an impactor stage of a miniaturized personal cascade impactor assembly.

FIG. 7 shows further detail of an outlet plate of a miniaturized personal cascade impactor assembly.

FIG. 8 shows a diagram of a personal pump that can be used with a miniaturized personal cascade impactor assembly.

FIG. 9 is a schematic of the experimental set-up used for the laboratory characterization of the PCIS.

FIG. 10 depicts a carrying pack that can be used to house and carry a pump and a miniaturized personal cascade impactor assembly.

FIG. 11 is a graph showing the pressure drop across PCIS as a function of flow rate.

FIG. 12 is a graph showing the collection efficiency of the 0.25 μm stage as a function of particle diameter.

FIG. 13 is a graph showing collection efficiency of the 0.50 μm stage as a function of particle diameter.

FIG. 14 is a graph showing collection efficiency of the 1.0 μm stage as a function of particle diameter.

FIG. 15 is a graph showing collection efficiency of the 2.5 μm stages as a function of particle diameter.

FIG. 16 is a graph showing particle losses in each of the PCIS stages.

FIG. 17 is a graph depicting the collection efficiency of the 0.25 μm stages as a function of particle mass loading.

FIG. 18 is a graph depicting the collection efficiency of the 1.0 μm stage as a function of particle mass loading.

FIG. 19 shows a graph depicting the collection efficiency curve for a 0.25 and 0.50 μm PCIS stage using ammonium nitrate as the test aerosol.

Like reference symbols in the various drawings indicate like elements.

DETAILED DESCRIPTION

Typically a cascade impactor has a plurality of collection stages arranged in series, with each stage comprising an impactor having a defined cutpoint range. In addition, each stage comprises a nozzle or orifice plate with nozzle openings smaller in size than those of a previous stage. The impactor surface comprises a defined cutpoint that serves to collect particles that are too large to be carried to the next stage in a gaseous sample stream (i.e., to the next impactor in the series). At each nozzle openings, the velocity of the gaseous sample is higher and the particles contained therein have a higher velocity moving through the nozzle. Typically the higher the flow velocity through the nozzle, the smaller the particles that are collected on the impactor surface. For example, particles comprising a diameter larger than a cutpoint of an impactor will impinge upon the impactor surface and the rest of the particles will pass with the gaseous stream to the next impactor in the series. The particles that are collected at each stage comprising an impactor can be analyzed by weight, or by quantitative chemical analysis. In some instances the particles may be chemically analyzed.

The Personal Cascade Impactor Sampler (PCIS) provided herein is a miniaturized cascade impactor, comprising four impaction stages, followed by an after-filter. Particles are separated in the following aerodynamic particle diameter ranges: <0.25, about 0.25 to 0.5, about 0.5 to 1.0, about 1.0 to 2.5, and about 2.5 to 10 μm. A 2.5 to 10 μm size range represents the coarse PM mode cutpoint. The 1 to 2.5 μm range is an intermediate mode cutpoint between coarse and fine PM. The 0.25 to 0.5 μm size cutpoint range represents particles typically created by accumulation of condensable material onto primary combustion particles. Particles rich in hygroscopic components such as ammonium sulfate and nitrate further grow to the 0.5 to 1 μm size when ambient relative humidity exceeds 60 to 70%. The 0.25 to 0.50 μm range and 0.5 to 1 μm range are sometimes referred to as "condensation" and "droplet" modes, respectively. The cutpoints were also chosen to progressively increase by a factor of 2 in order to facilitate logarithmic plots of aerosol size distributions determined with the PCIS.

A cutpoint defines a size or range of size of particulate matter (PM) wherein any PM size larger than the defined cutpoint is substantially removed from a gas sample, while particles with sizes less than the define PM size pass through to a next level (e.g., the next filter or impactor). For example, a 10 μm cutpoint impactor or filter will remove 50% of the particles with size equal to 10 μm from a gas sample while 50% of the particles with size equal to 10 μm pass through the impactor or filter.

As used herein a gas sample comprises atmospheric or ambient air from indoor and/or outdoor sources.

FIGS. 1A and B collectively shows a miniaturized cascade impactor comprising four impaction stages, followed by an after-filter. With reference to FIG. 1A there is shown a miniaturized cascade impactor assembly 50 having a first end comprising an inlet 100, a plurality of orifice plates 120 and a plurality of impactor stages 140. The final stage in the miniaturized cascade impactor assembly comprises an after filter 160. The miniaturized cascade impactor assembly 50 is shown as being substantially rectangular with each stage and plate being rectangular, however other shaped stages and plates can also be used (e.g., substantially circular thereby rendering a cylindrical assembly). The various stages and plates may comprise an o-ring or similar method to seal the stages and plates to one another. In addition, the stages and plates may be sealably fastened together by clamps, screws, bolts and nuts, as well as threaded members at the ends of each stage and plate.

FIG. 1B shows the miniaturized cascade impactor assembly in individual segments. The miniaturized cascade impactor assembly 50 comprises a first plate 180 having an inlet 100 for receiving a gas sample. Orifice plates 120 comprise orifices 200 that allow the gas sample comprising the particulate matter through to impactor stages 140. Each orifice 200 in each orifice plate 120 becomes smaller the further from the inlet 100. The orifices 200 are depicted here as being substantially rectangular although round nozzles may also be implemented in the current invention. The change in size of the orifices 200 maintains a proper velocity of the gas sample comprising the particulate matter as the gas sample flows through the miniaturized cascade impactor assembly. Each impactor stage 140 comprises impactor surface 220. Impactor surface 220 will vary in composition and/or size to separate out the various sizes of particulate matter and related components.

The miniaturized cascade impactor assembly 50 may be further housed in a protective housing. In addition, a pre-separator may be fluidly connected before inlet 100 to separate out large particles. The internal volume of the miniaturized cascade impactor assembly 50 is relatively small. For example, the internal volume is about 200 cm$^3$.

FIG. 2 shows an orifice plate 120 and impactor stage 140 in more detail. An impactor stage 140 comprises an impactor surface 220 having a desired cutpoint, one or more o-rings 240 located on either side of each stage, and connection holes 260. As described herein, the impactor surface 220 comprises cutpoints ranging from 2.5–10 $\mu$m to <0.25 $\mu$m. For example, the impactor surface closest to inlet 100, will comprise an impactor surface 220 having a cutpoint of about 2.5 to 10 $\mu$m. The impactor surfaces in the direction of gas sample flow become smaller as the gas proceeds through the miniaturized cascade impactor assembly. For example, the first impactor surface comprises a cutpoint of about 2.5 to 10 $\mu$m, the second impactor surface in the series comprises a cutpoint of about 1.0 to 2.5 $\mu$m, the third impactor surface in the series comprise a cutpoint of about 0.5 to 1.0 $\mu$m, the fourth impactor surface comprises a cutpoint of about 0.25 to 0.5 $\mu$m, and the final stage comprises a filter that filters particulate matter <0.25 $\mu$m.

Figure 3C:
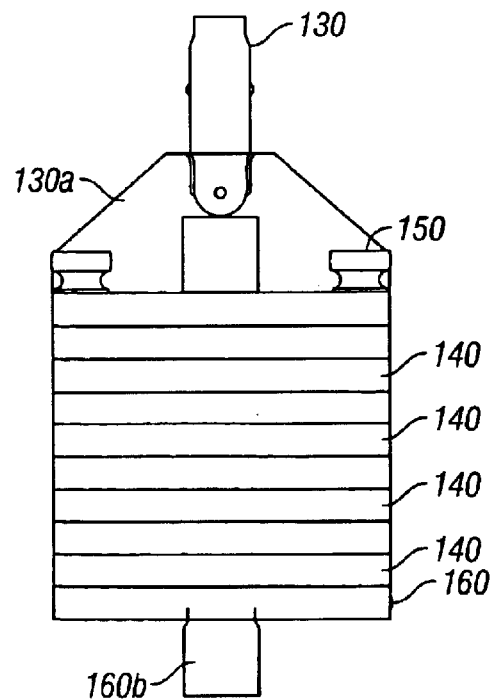
Figure 4A:
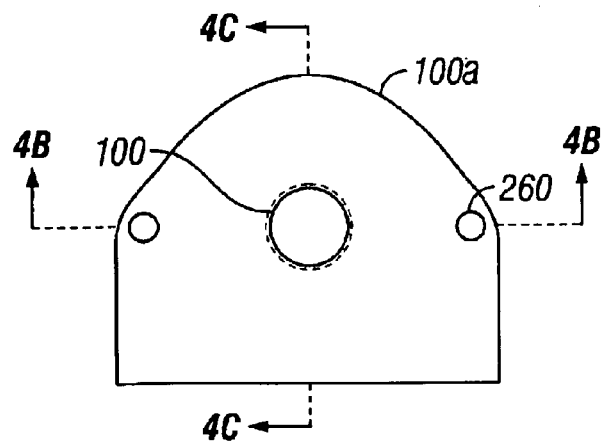
Figure 4B:
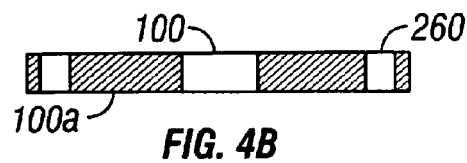
Figure 4C:
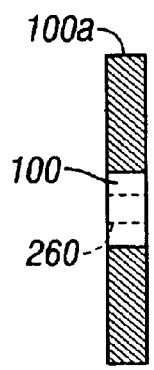
Figure 4D:
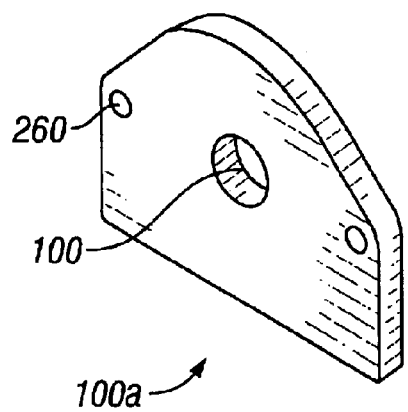
Figure 5A:
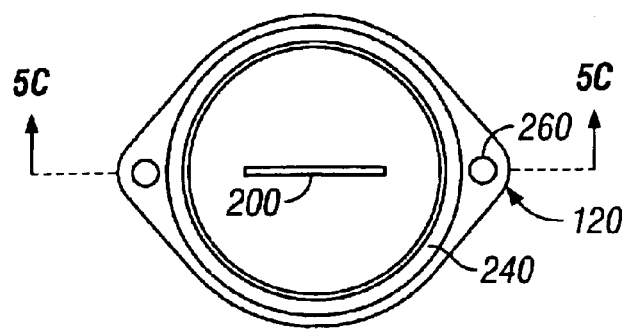
Figure 5B:
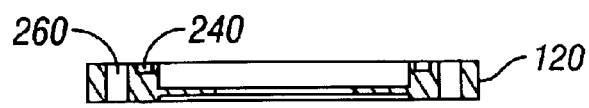
Figure 5C:
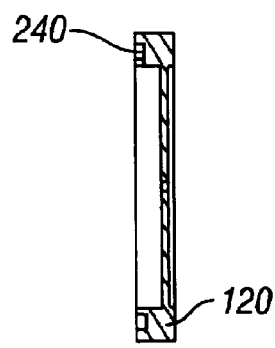
Figure 5D:
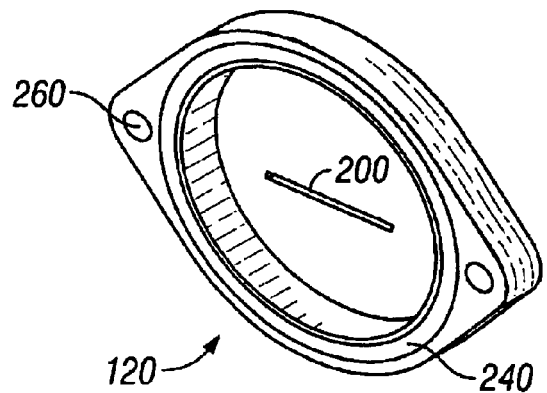
Figure 6A:
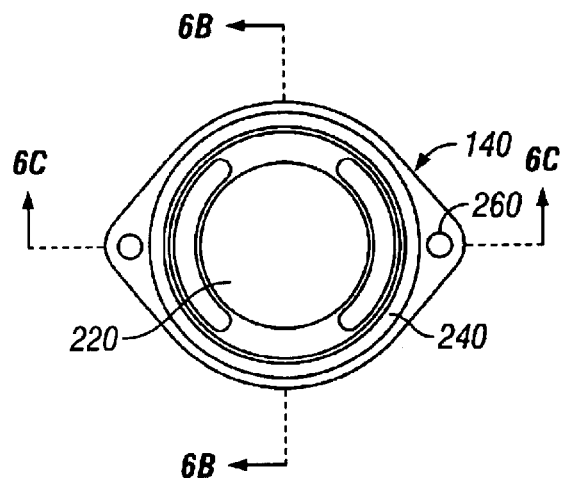
Figure 6C:
Figure 6B:
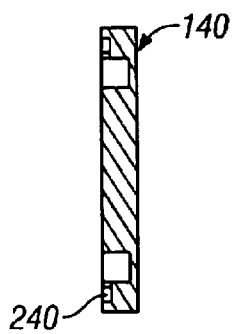
Figure 6D:
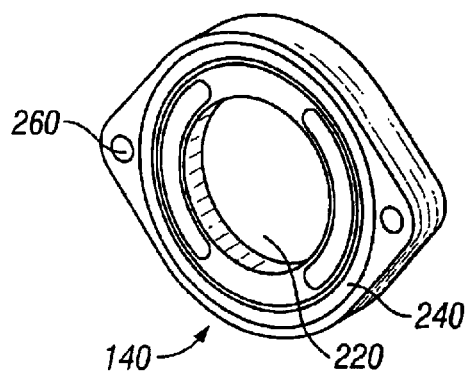
Figure 7A:
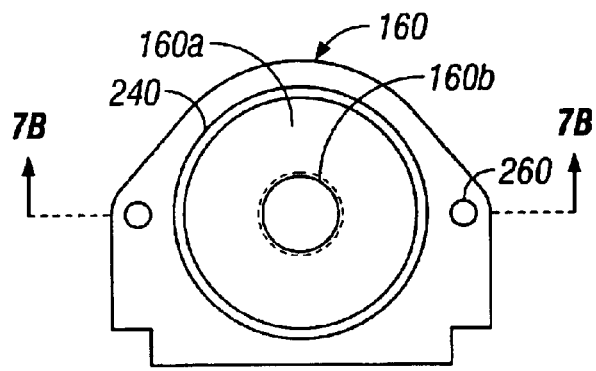
Figure 7B:
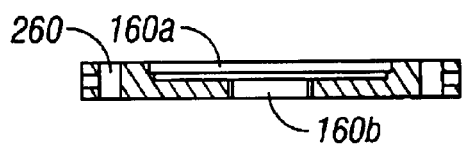
Figure 7C:
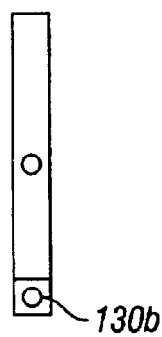
Figure 7D:
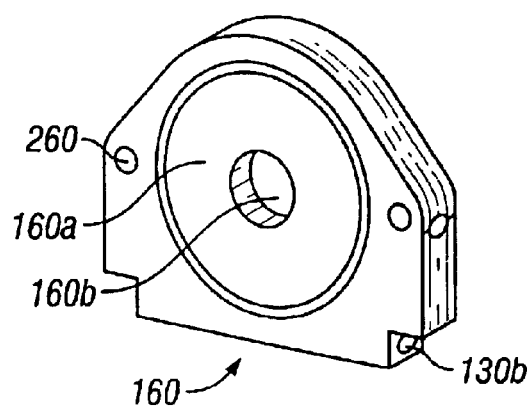
Figure 8:
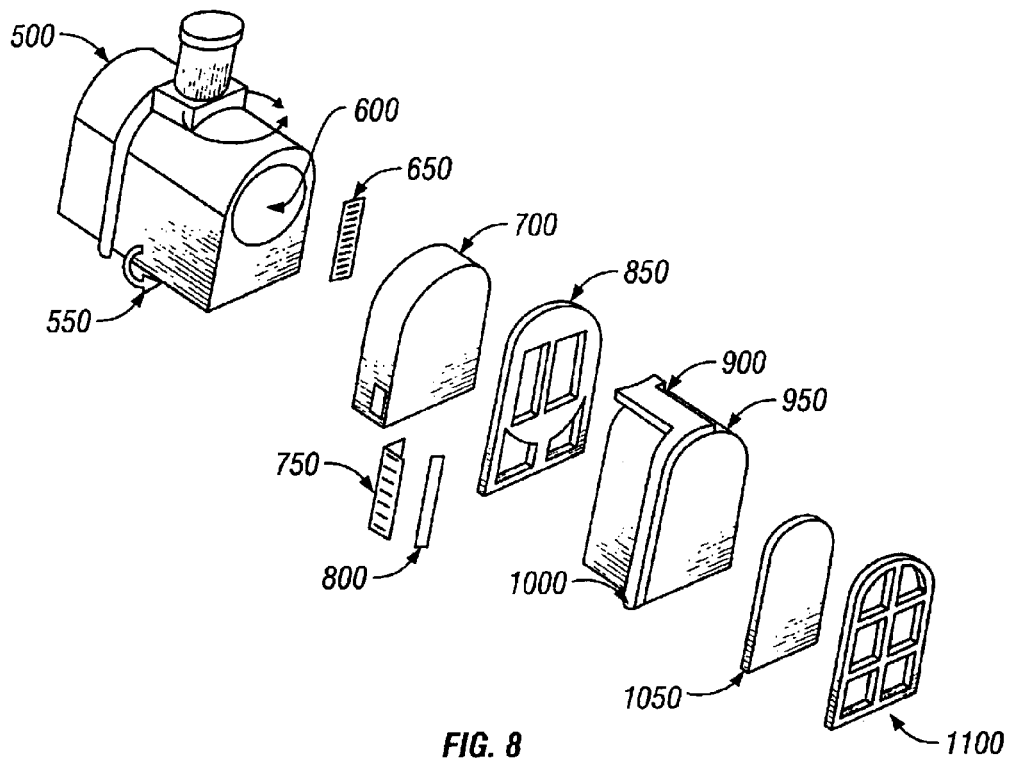

FIG. 3 shows an impactor assembly of the invention. With reference to FIG. 3A there is shown a miniaturized cascade impactor assembly 50. FIG. 3B and C show assembly 50 from a side and frontal view, respectively. The miniaturized cascade impactor assembly 50 comprises an attachment clip 130, for attachment of the PCIS to a personal item such as clothes, a belt, and the like. Attachment clip 130 may comprise a loop for slipping over and around a belt, a hook for hooking to a belt loop, and the like. Also shown is attachment plate 130a which associates the attachment clip 130 with assembly 50. Hinge portion 130b is also depicted and comprises a movable hinge attached to plate 130a. Rotating hinge 130b causes the plate 130a to be separated from the assembly 50 and allows for disassembly of the PCIS of the invention. Nuts 150 attach to bolts which slip through each stage or plate of the assembly to securely hold the plates and stages of the assembly together during operation.

FIG. 4 shows inlet plate 100a in more detail. Inlet plate 100a comprises an inlet 100 and connection holes 260. The connection holes may be threaded for receiving a threaded screw or bolt or may be non-threaded for receiving a shaft portion of a bolt. Also shown in view A—A are holding plate attachment holes. These attachment holes assist in holding the attachment plate 130a to assembly 50.

FIG. 5 shows orifice plate 120 in further detail. The orifice plate 120 comprises connection holes 260 for receiving a threaded or shaft portion of a bolt, an o-ring 240 and a rectangular orifice 200. The orifice 200 of each orifice plate 120 in the assembly 50 may vary in size as discussed herein.

FIG. 6 shows an impactor plate in further detail. Impactor plate 140 comprises connection holes 260 for receiving a threaded or shaft portion of a bolt, an o-ring 240 and an impactor surface 220. The impactor surface 220 will comprise a filter or other material having a desired cutpoint size for collection of particulate matter.

FIG. 6 shows the filter stage 160 in further detail. The filter stage 160 comprises connection holes 260, outlet 160b, recess 160a for receiving a filter or filter device, and o-ring 240. The filter can be inserted within recess 160a or may be located within a removable frame member wherein the frame member comprising the filter fits into recess 160a. Also shown in FIG. 6 is hinge location 130b. The hinge may be designed such that a shaft member slides through holes located at 130b, alternatively a pin (e.g., a spring-loaded pin) may be located at 130b. The hinge attaches to attachment plate 130a.

The sampling flow rate of a PCIS of the invention is about 9 L/min(LPM) and the measured total pressure drop across the sampler is about 8 to 15 inches of water, but is typically on the order of about 11 inches of water (2.7 kPa). The lower pressure drop makes it possible to operate the sampler with a very low noise level, which is a desirable feature in personal monitoring. The entire miniaturized cascade impactor assembly can be enclosed in a cassette holder or other housing, 4 cm in diameter and 6 cm in height, made of a soft aluminum or similar material in order to avoid particle losses due to electrostatic deposition.

The flow path in the miniaturized cascade impactor assembly is shown essentially in FIG. 1B by arrow 110. The flow path is from the inlet 100 through filter stage 160. The path traverses the impactor stages 140 and orifice plates 120.

The number of impactor stages and orifice plates may be varied. Depicted in the figures are 4 impactor stages and 4 orifice plates, however more or fewer impaction stages may be used with various cutpoints depending upon the data one desires to collect. Typically the nozzles and the orifice sizes are selected to provide at least 4 cutpoints at all desired flow ranges that are between 0.25 $\mu$m and 10.0 $\mu$m (excluding the filter stage at the distal end of the assembly). In addition, the first stage should provide a cutpoint for particles between 2.5 $\mu$m and 10 $\mu$m. A pressure drop across the impactor of less than 12 inches of water at the maximum flow rate is desired.

In one aspect of the invention, the assembly provides fixed orifice plates and flow rates of about 5 to 12 liters per minute (LPM), but typically are about 9 LPM. The cutpoint of particles at the first impactor stage with a flow rate of 9

LPM will provide particles of about 2.6 µm. The cutpoint of the last stage (excluding the filter stage) at a minimum design flow rate of 9 LPM is 0.23 µm.

The orifice stages and sizes are spaced appropriately to maintain a velocity of about 550–650 cm/s prior to the first impactor stage, typically on the order of 630–660 cm/s, but preferably average about 645.5 cm/s. The orifice stage immediately prior to the second impactor stage should provide a velocity of about 1800–2200 cm/s, typically on the order of 1950–2050 cm/s, but preferably average about 2041.2 cm/s. The orifice stage immediately prior to the third impactor stage should provide a velocity of about 1900–2200 cm/s, typically on the order of 2000–2150 cm/s, but preferably average about 2110.0 cm/s. The orifice stage immediately prior to the fourth impactor stage should provide a velocity of about 4000–5000 cm/s, typically on the order of 4200–4800 cm/s, but preferably average about 4568.8 cm/s. If the orifice stages are too close to each other or to the impactor surface of the impactor stage, they will tend not to collect particulate matter well. The dimensions of the rectangular orifices in each orifice plate are about 0.014–0.09 cm×1.9–2.5 cm. In certain embodiments, the dimensions of each orifice in each orifice plate are:

| STAGE # | length × width |
|---|---|
| Stage 1 | 1.9 cm × 0.09 cm |
| Stage 2 | 2.1 cm × 0.05 cm |
| Stage 3 | 1.9 cm × 0.036 cm |
| Stage 4 | 2.5 cm × 0.014 cm |

The mechanisms determining capture of particulate matter include (A) interception of particles whose size is comparable to the pore size; (B) impaction of large particles on the filter surface due to deflection of the gas stream; (C) diffusion of small particles to the pore walls; (D) retention of particles larger than the pores (sieve effect); and (E) electrostatic effects (Spurny et al., Environ. Sci. Tech., 3(5):453–468, 1969). Electrostatic effects are overcome by the invention by utilizing materials (e.g., aluminum) that have a reduced, negligible, or non-existent electrostatic potential.

Design of the impactor stages are based upon the Stokes number of a particle having a 50% probability of impacting, $St_{50}$ defined as:

$$St_{50} = \frac{\rho_p d_{50}^2 U C_c}{9\mu D} \tag{1}$$

where $d_{50}$ is the geometrical diameter of a particle having a 50% probability of impacting, U is the average velocity of the jet (cm/s), D is the impactor's nozzle diameter (round nozzle) or width (rectangular nozzle), $\rho_p$ is the particle density (g/cm$^3$), $\mu$ is the dynamic viscosity of the air (g/cm s), and $C_c$ is the Cunningham slip correction factor.

The slip correction factor is given by the equation:

$$Cc = 1 + \frac{2}{Pd_p}[6.32 + 2.01\exp(-0.1095Pd_p)] \tag{2}$$

where P is the absolute pressure upstream of the impaction zone (in cmHg) and $d_p$ is the particle diameter in $\mu$m.

The impactor surfaces (e.g. filters) present in the assembly can be designed based upon the teachings herein as well as those known in the art. In particular, the pressure drop at each filter should be designed to provide the highest collection efficiency with the least pressure drop.

The miniaturized cascade impactor assembly described above can be attached to a small pump that is easily carried by a person in everyday activities. FIG. 8 shows and example of a pump useful in the invention. With reference to FIG. 8 there is shown generally a personal pump comprising a pump body 500 ,a fixing clip 550 above and below the pump body 500, and a diaphragm 600 housed within the pump body. Exhaust valve 650 is located between diaphragm 600 and valve plate 700. The exhaust valve comprises a valve diaphragm 750 and retainer 800. A gasket 850 sealably fits between the valve plate 700 and a flow sensor take-off member 900 comprising an end cap 950. A flow sense tube 1000 is fluidly connected to the flow sensor take-off 900. A pulsation dampener 1050 fits within end cap 950 and cover 1100 securely holds the pulsation dampener 1050 to the end cap 950.

The personal pump is a dual diaphragm pump, in which rotational energy from a small DC motor is converted to linear motion by a shaft mounted eccentric bearing and connecting rod assembly, to drive the two pumping diaphragms. The diaphragms are molded from a rubberized material and operate with a rolling motion rather than stretching to minimize power requirements. Each pumping chamber contains inlet and exhaust valves, which respond to the pressure changes in the pump chambers during the pump stroke and require no physical actuation. The valve in the pump is designed to minimize the pressure required for opening and closing, hence the power requirements, as well as to reduce noise. Both the inlet and exhaust paths of the pump mechanism utilize dampener chambers to reduce pulsation in the airflow caused by the cyclic nature of the pump operation. The rigid sections of the pump can be injection-molded from thermoplastic material to provide strength and light weight.

A battery and/or solar element can be used to provide the electric needs of the pump. For example a battery pack can comprise 10 lithium-ion rechargeable cells arranged in a series/parallel arrangement to give a nominal voltage of 7.2 V with a capacity of 9 Amp hours. The battery pack can be located within the PCIS such that quick removal and replacement can be made if time is not available for recharging. A pump case can also be provided to encase the pump within a protective noise deadening material. Such a case can be molded using a two shot process, which allows the body to be molded in hard plastic with an over-molding of a softer material in certain sections. A softer rubber-like material can be used to form a buffer around the edges of the case to protect against damage as well as help with noise reduction.

The PCIS of the invention can comprise a microprocessor that enables data storage within the personal pump. The microprocessor makes correction for temperature and atmospheric pressure changes allowing the pump to be calibrated in terms of volumetric flow as required for operation with the PCIS.

EXAMPLES

A PCIS was assembled as described herein and with reference to the figures. The miniaturized cascade impactor assembly weighed approximately 150 g, thus easy to be used by subjects such as children or elderly. The pump weighs about 450 g (including the battery) and is placed inside a small pouch with snap latch and foam inserts to protect the pump during transport and use.

The design and operation parameters of each impaction stage are shown in Table 1 (below). The 50% cutpoint is estimated from the collection efficiency curves of each impaction stage, which are described herein. Particles in the size range of 0.25–10 µm are accelerated in rectangular-shaped nozzles and collected on commercially available 2.5 cm filter substrates made of quartz (Pallflex Corp., Putnam, Conn.), PTFE (Teflon®)(3 µm pore, Gelman Science, Ann Arbor, Mich.) or aluminum foil disks that serve as the impaction substrate. In each stage, the impacted particles are collected on a small surface area of about 1 $cm^2$ or less of these 2.5 cm filter substrates. This is a substantially smaller surface area compared to the 13.8 $cm^2$ area of a standard 4.7 cm filter found in prior cascade impactors. The reduced area of impaction and particulate deposition make it possible to use smaller liquid extraction volumes for certain types of chemical analysis of the particulate matter (e.g., ion chromatography, inductively coupled plasma-mass spectroscopy), thereby decreasing the limit of detection. Particles smaller than 0.25 µm, are collected on a 3.7 cm filter in the final stage of the assembly (2 µm pore, Gelman Science, Ann arbor, Mich.).

TABLE 1

Design and operating parameters of the PCIS (flow rate: 9 LPM)

| Design impaction cutpoint (µm) | Experimentally determined cutpoint (µm)[e] | $D^a$ (cm) | $D^b$ (cm/s) | $\Delta P^c$ (in $H_2O$) | $L^d$ (cm) |
|---|---|---|---|---|---|
| 2.5 | 2.60 | 0.09 | 645.5 | 0.3 | 1.9 |
| 1 | 0.95 | 0.05 | 2041.2 | 0.6 | 2.1 |
| 0.5 | 0.52 | 0.036 | 2110.0 | 1.5 | 1.9 |
| 0.25 | 0.23 | 0.014 | 4568.8 | 3.9 | 2.5 |
| Teflon Filter | — | 3.7 | 10.3 | 4.7 | — |

[a]Acceleration slit nozzle width of each jet.
[b]Average jet velocity.
[c]Pressure drop (measured for all stages and after-filter).
[d]Length of the acceleration jet (also length of the deposit).
[e]Estimated from the collection efficiency curves shown in FIGS. 12 to 15 and for the PTOFE (Teflon) impaction substrate.

Figure 9:
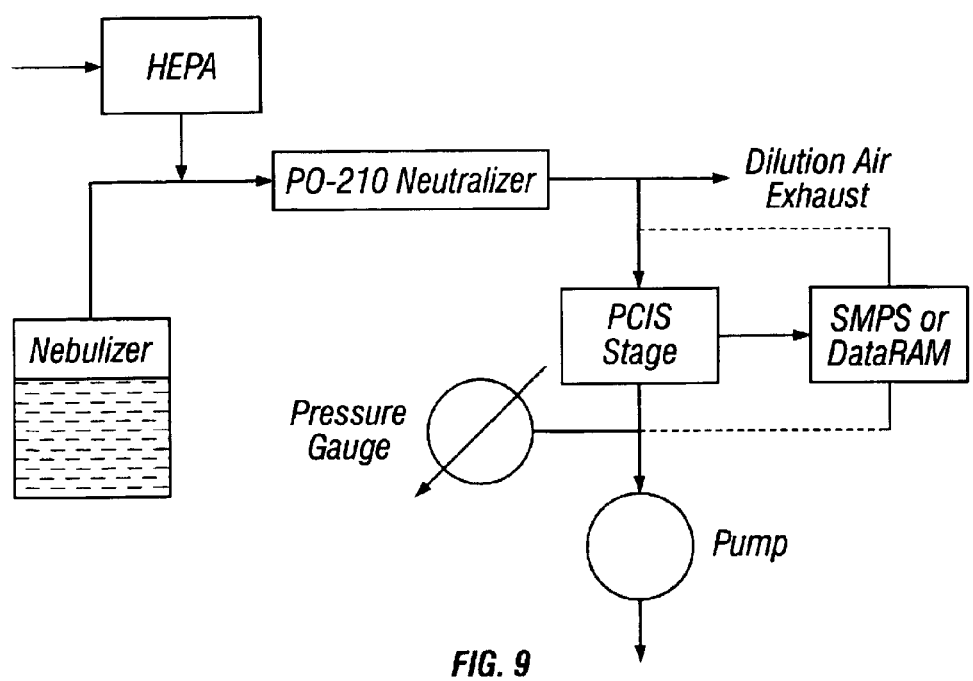
Figure 10:
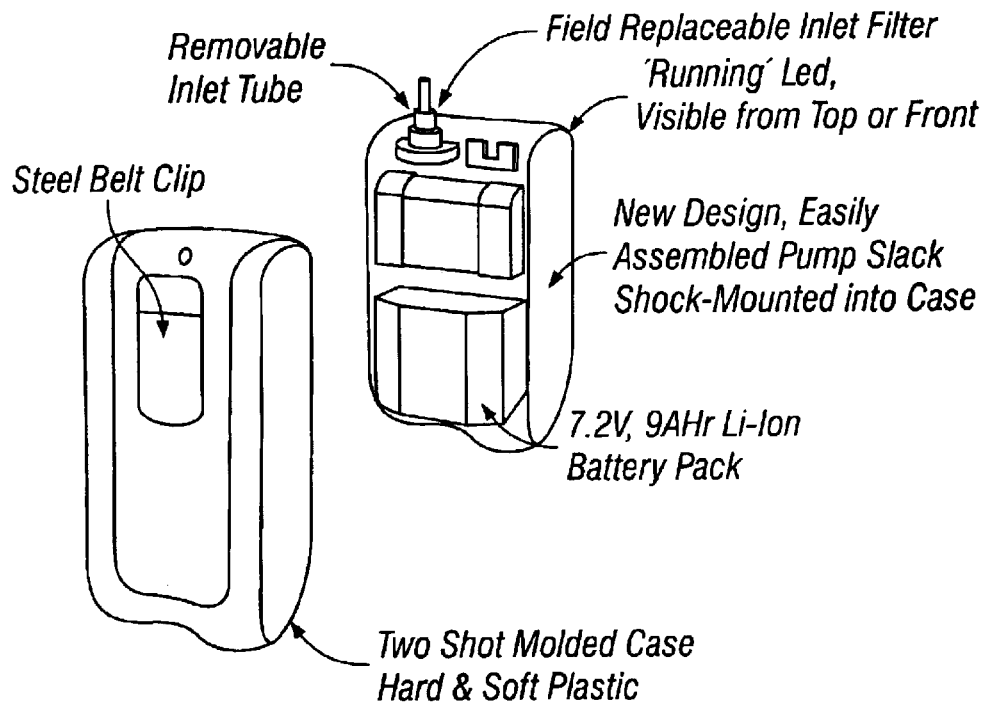

The particle collection efficiency as a function of particle size for the 0.25, 0.50, 1.0, and 2.5 µm cutpoint stages were determined using polydispersed ammonium sulfate aerosols generated by means of a nebulizer (HOPE, B&B Medical Technologies, Inc., Orangevale, Calif.). The experimental set-up is shown schematically in FIG. 9. Aqueous ammonium sulfate solutions (roughly 1 mg of ammonium sulfate in 1 ml of deioinized water) were nebulized using room air at 20 psi. The generated aerosol passed through a 1 liter chamber with twin Polonium 210 ionizing units (Staticmaster, NRD Inc., Grand Island, N.Y.) to reduce particle charge close to the Boltzmann equilibrium. After the neutralizer, the aerosol was mixed with room air (relative humidity: 20–30%) in a 35 L mister chamber and passed through a specific impaction stage. For particles in the size range of 0.015–0.8 µm, penetration (or collection efficiency) was determined by measuring their number concentration upstream and downstream of the impactor by means of the Scanning Mobility Particle Sizer (SMPS, Model 3096, TSI Inc., St. Paul, Minn.). The SMPS sampled 0.3 LPM of the total flow rate of 9 LPM through the impactor. The PCIS flow rate was monitored continuously throughout the experiments using a calibrated in-line direct-reading flow meter (Model EW-32448-54, Cole-Parmer Instrument Company, Vernon Hills, Ill.).

In addition to the SMPS, the DataRAM (RAM-1, MIE Inc., Billerica, Mass.) was used to evaluate the collection efficiency of the 0.50, 1.0, and 2.5 µm stages for particles in the 0.2–10 µm range, using laboratory-generated monodisperse polystyrene latex (PSL) particles (Bangs Laboratories Inc., Fisher Ind.) in a process otherwise identical to that described above in the SMPS tests. The DataRAM could not be used to monitor particles less than 0.2 µm, because the sensitivity of the instrument decreases sharply below this particle size, whereas the SMPS could not be used for particles larger than approximately 0.8 µm since they are removed by the impactor placed in the inlet of the instrument.

Each PCIS stage was evaluated using the following surfaces as impaction substrates:

(a) 2.5 cm quartz filter (b) 2.5 cm aluminum foil disk (c) 2.5 cm PTFE filter (d) 2.5 cm quarts filter coated with a thin layer of mineral oil (for the 0.25 µm stage only).

Impaction surfaces (a)–(c) were used without any coating or adhesive material for all PCIS stages. For the 0.25 µm cutpoint stage, the collection efficiency as a function of particle size obtained for the coated quartz substrate was compared to those of the uncoated substrates to determine the degree to which particle bounce occurs. These experiments were only conducted for the 0.25 µm PCIS stage because the higher impaction jet velocity of that stage would increase the likelihood of particle bounce.

Figure 11:
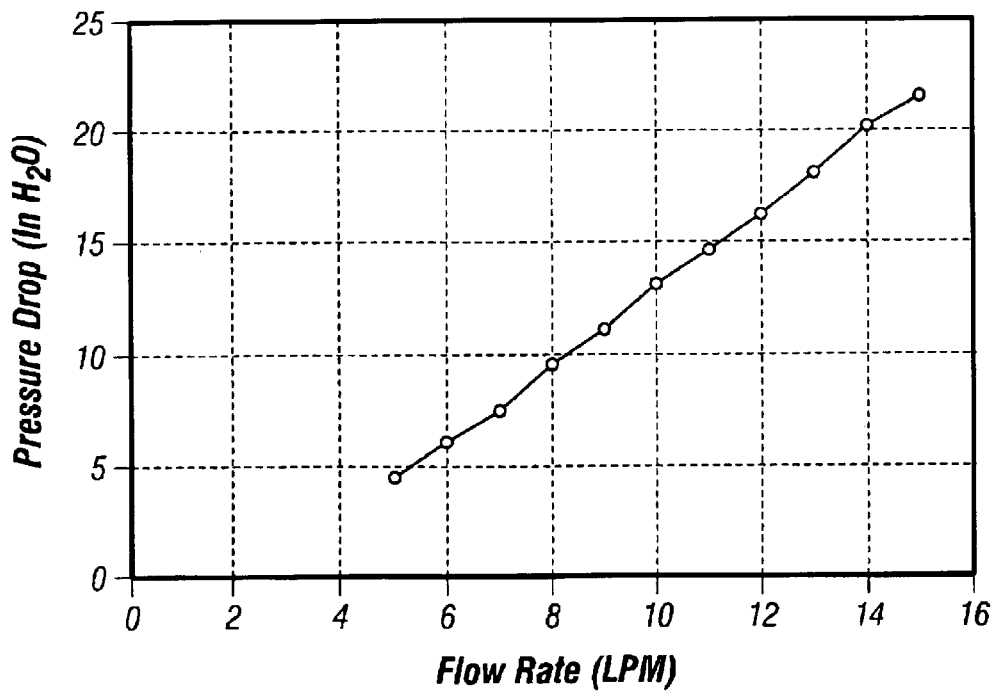
Figure 12:
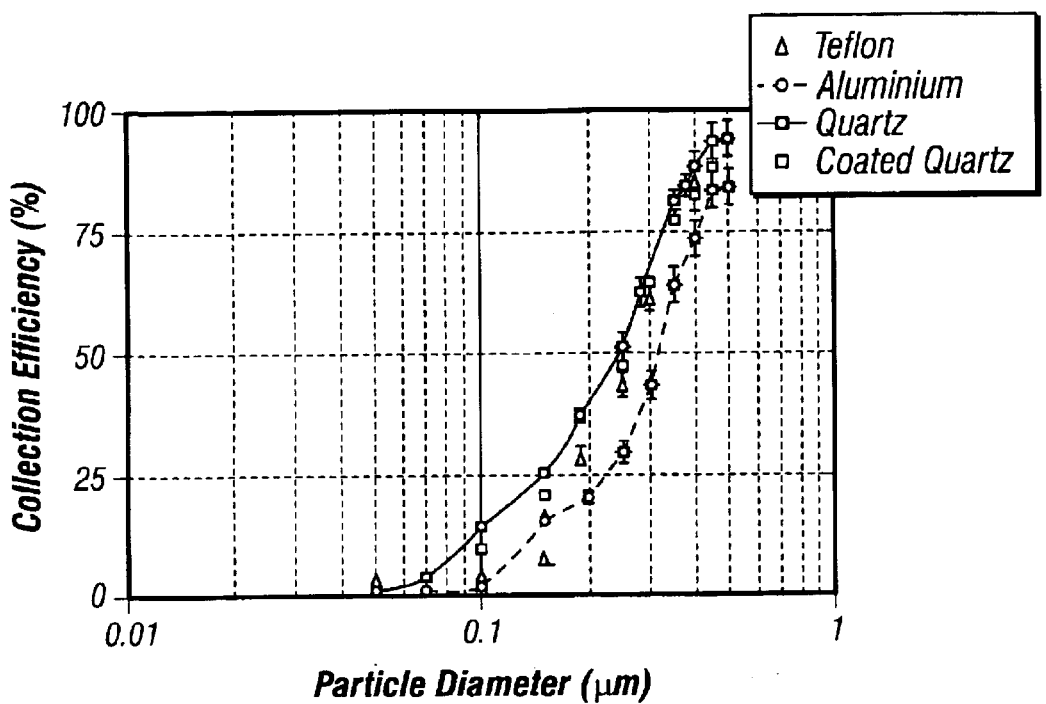

A plot of the pressure drop across the entire PCIS as a function of the sampling flow rate, including all of the four impactor stages and the 3.7 cm Teflon after-filter, is shown in FIG. 11. Pressure drop measurements were recorded for flow rates ranging from 5 to 15 LPM using a Magnehelic (Dwyer Instruments, Inc., Michigan City, Ind.). The targeted sampling flow rate is between 9 and 10 LPM and the corresponding total pressure drop across the sampler is found to be 11–13 in of $H_2O$. Based on these results and the specifications of the personal pump, the PCIS can operate at this flow rate range for at least 24 hours without any need for re-charging of the battery of the pump.

Results from the evaluation test of the 0.25, 0.50, 1.0, and 2.5 µm stages are summarized in FIGS. 12–15, respectively. Particle collection efficiency data for each stage are plotted as a function of aerodynamic particle diameter. The collection efficiencies using three different surfaces as impaction substrates are shown in the same graph for direct comparison. The results plotted in FIG. 12 for the 0.25 µm cutpoint stage indicate that there is no substantial difference between the coated quartz, and the uncoated PTFE and quartz impaction substrates. All three substrates have the same 50% collection efficiency cutpoint, approximately at 0.22–0.23 µm in aerodynamic diameter, thus very close to the design cutpoint. Particle collection efficiency increases rapidly to higher than 85% for particles 0.35 µm and above. No test were conducted for particles larger than 0.5 µm because they are presumably collected by a preceding impaction stage, which has a 50% cutpoint at that size. The slope of the collection efficiency curve obtained for PTFE is slightly steeper than those obtained for the coated and uncoated quartz substrates. This may be due to capture of particles smaller than the cutpoint on the fibrous quartz surface because of partial entrainment of the impinging jet streamlines on the surface. By contrast, PTFE is a relatively harder impaction surface and this entrainment should be minimal. The good overall agreement between the collection efficiencies of the coated and uncoated quartz and PTFE substrates suggests that the use of coating, which would minimize particle bounce would substantially complicate chemical analysis of the collected particulate matter, is not necessary. An example of the effect of particle bounce on the collection efficiency values for any particle size obtained for the substrate can be attributed to particle bounce.

Figure 13:
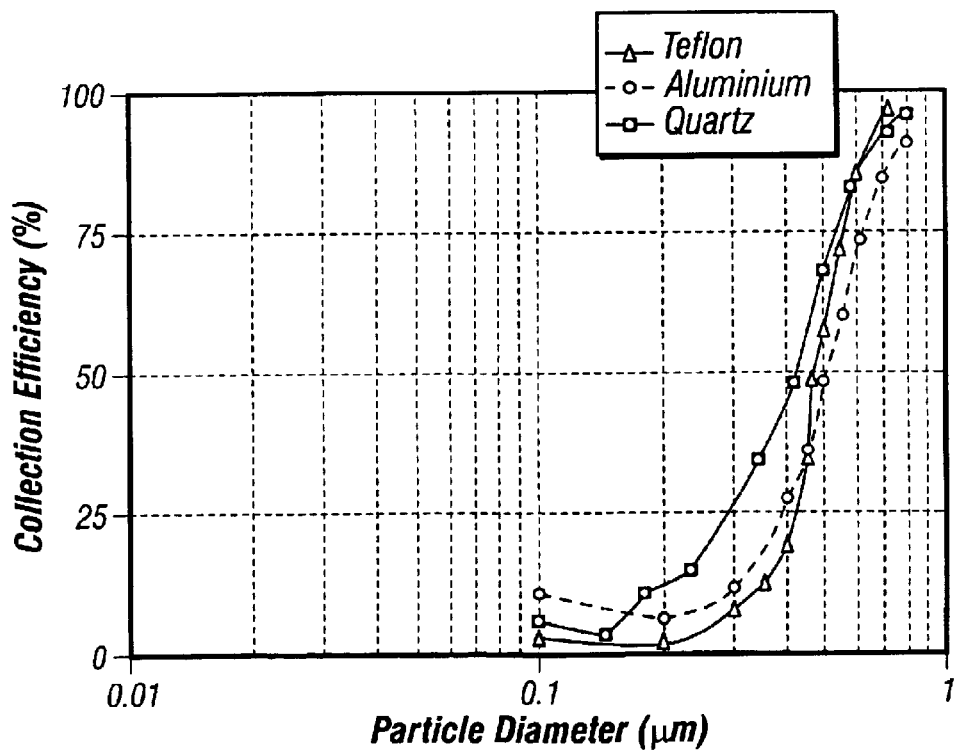

The results plotted in FIG. 13 for the 0.50 µm cutpoint stage indicate that the 50% collection efficiency cutpoint is approximately 0.48–0.50 µm in aerodynamic diameter, for the Teflon and aluminum substrates, thus very close to the design cutpoint. Particle collection efficiency becomes higher for the quartz substrates, particularly for particles smaller than the design (or theoretical) cutpoint of that stage, including the actual 50%, which for this substrate was estimated to be at 0.43 µm. Particle collection efficiency increases rapidly to higher than 85% for particles 0.60 µm and above for the quartz and Teflon substrates. Furthermore, the slope of the collection efficiency curve obtained for PTFE and aluminum substrates is slightly steeper than those obtained for the quartz substrate. Similar to the results obtained for the 0.25 µm PCIS stage, the increased efficiency and decreased steepness of the quartz substrates are due to capture of particle smaller than the cutpoint on the fibrous surface because of partial entrainment of the impinging jet streamlines on the fibrous surface. Particle collection efficiency also decreased for particles larger than the cutpoint of this stage when the aluminum substrate was used, probably due to some particle bounce on that surface which would be more pronounced for particles larger than the cutpoint. This phenomenon is more likely to occur in the aluminum substrates because of the higher surface hardness of aluminum compared to Teflon or quartz.

Figure 14:
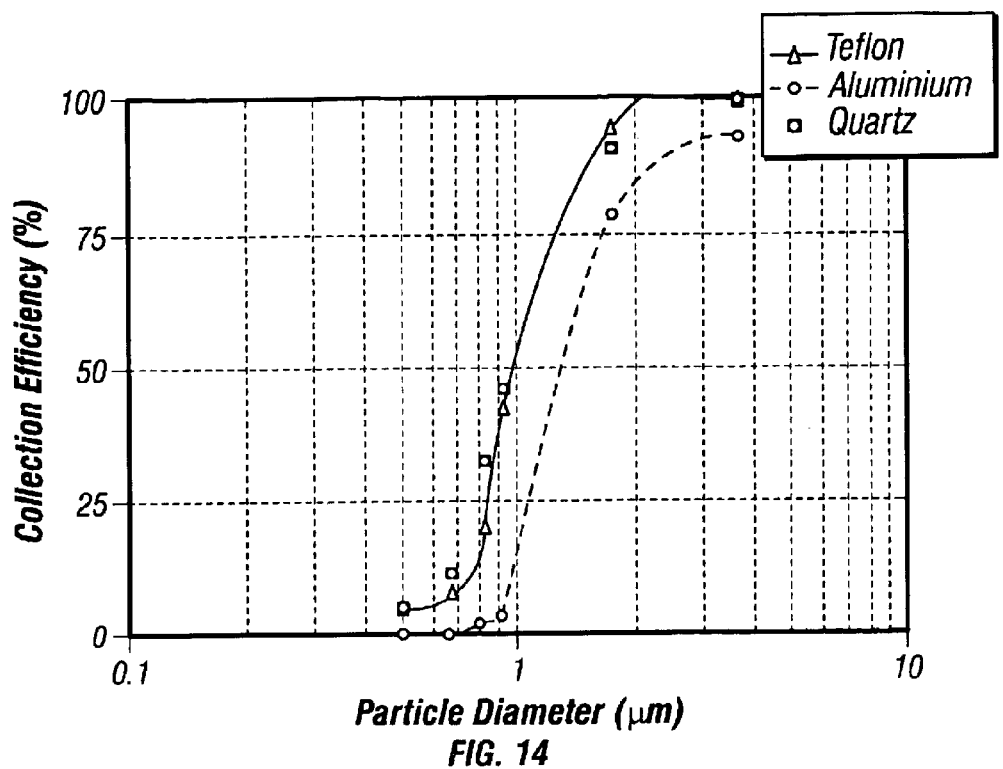

Results from the evaluation of the 1.0 µm stage are shown in FIG. 14. The collection efficiency curves for quartz and Teflon substrates are quite similar, whereas the efficiencies obtained for the aluminum substrates seem to be substantially lower—similar to the results observed for the 0.25 and 0.50 µm stages. Again, the decreased collection efficiency observed for aluminum can be attributed to particle bounce onto the harder surface of this substrate. There are no quartz substrates, as both surfaces lead to the same cutpoint (1.0 µm). By comparison, the 50% cutpoint obtained with aluminum substrate was closer to 1.5 µm.

Figure 15:
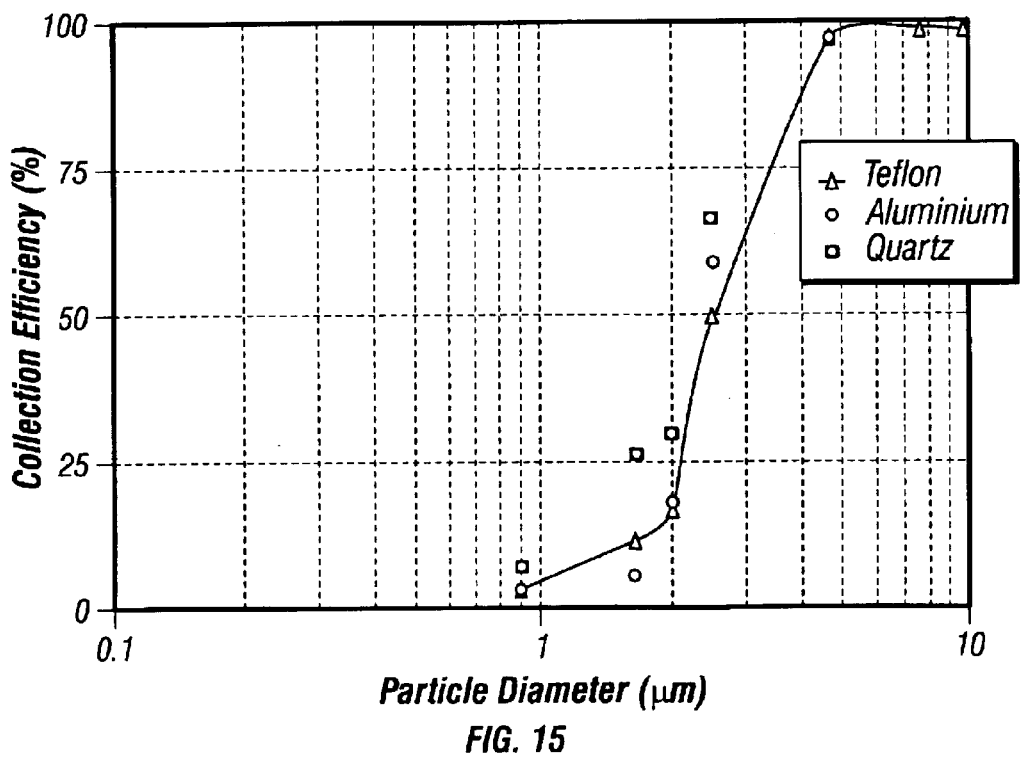

The particle collection efficiency as a function of aerodynamic diameter for the 2.5 µm stage of the PCIS is shown in FIG. 15 for different impaction substrates. The plotted data indicate that collection efficiency trends vs. particle size are quite similar for the three substrates. Contrary to the observations made for the 0.25, 0.50, and 1.0 µm PCIS stages, particle bounce seems to be less pronounced for the aluminum substrates in this stage, given the high collection efficiency observed for particles larger than 2.5 µm. This is likely due to the substantially lower impactor jet velocity of this stage (Table 1, above).

The sharpness of the collection efficiency curve of an impactor can be defined in terms of the geometric standard deviation ($\sigma_g$), which is the square root of the ratio of the aerodynamic particle diameter corresponding to 84% collection efficiency to that corresponding to 16% efficiency (Marple and Willeke, 1976). Based on this definition, the values for $\sigma_g$ for each stage and substrates were estimated and listed in Table 2, below. Generally, lower $\sigma_g$ values indicate the higher precision in particle separation characteristics of a given impaction stage, which is highly desirable feature of an impactor as it leads to a finer resolution in the size distribution of an aerosol. Based on this definition, the value of $\sigma_g$ is approximately 1.2–1.3 for the PTFE and aluminum substrates, thereby indicating reasonably sharp aerodynamic particle separation characteristics when these two substrates were used. The value of $\sigma_g$ increase to about 1.5 for the quartz substrate, especially for the lower cutpoint stages of the PCIS, because of the increased collection efficiency observed for this type of substrate for particles smaller than the theoretical cutpoint of the impactor.

TABLE 2

Sharpness of the collection efficiency for each stage of the pCIS as a function of substrate

| Substrate type | PCIS stage (µm) | Geometric standard deviation ($\sigma_g$) |
|---|---|---|
| PTFE (Teflon) | 0.25 | 1.28 |
| Quartz | | 1.53 |
| Aluminum | | 1.31 |
| PTFE (Teflon) | 0.50 | 1.25 |
| Quartz | | 1.58 |
| Aluminum | | 1.39 |
| PTFE (Teflon) | 1.0 | 1.25 |
| Quartz | | 1.32 |
| Aluminum | | 1.34 |
| PTFE (Teflon) | 2.5 | 1.19 |
| Quartz | | 1.39 |
| Aluminum | | 1.22 |

Figure 16:
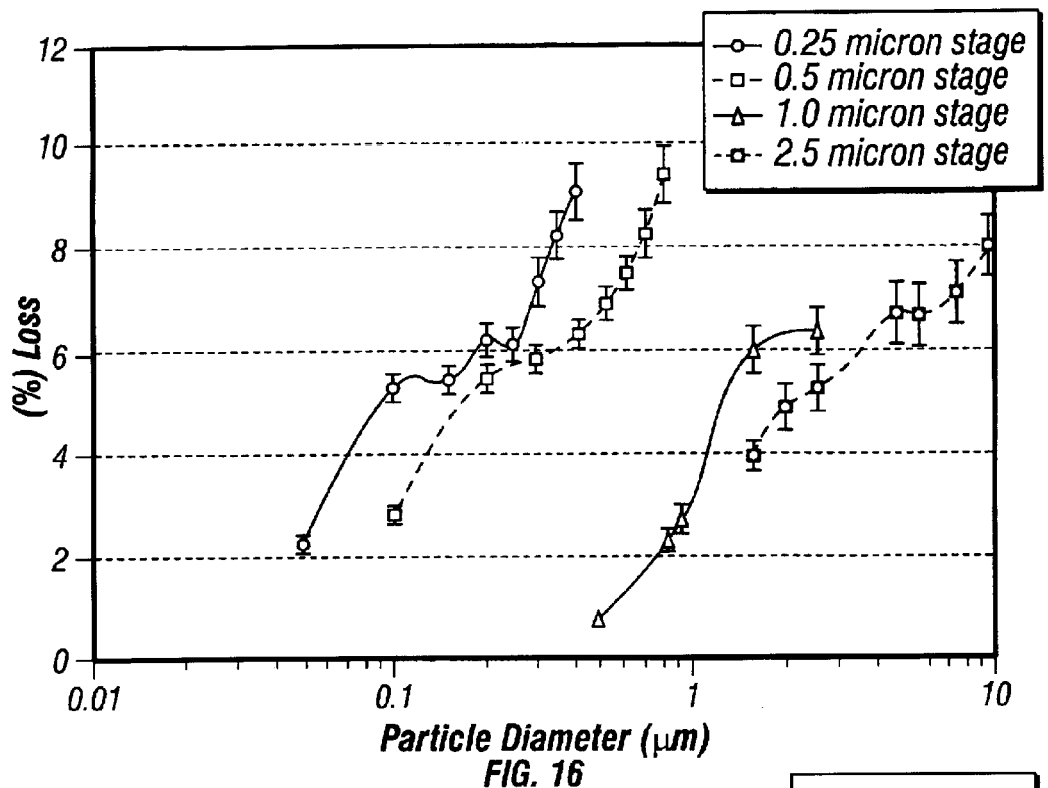

Particle losses in each PCIS stage, shown in FIG. 16, were evaluated by first removing the impaction substrate block of that stage and by measuring the concentrations of the polydisperse ammonium sulfate (0.05–0.5 µm), or monodisperse (0.2–10 µm) PSL particles upstream and downstream of the stages using the SMPS and dataRAM, respectively. As evident from the figure, losses in each PCIS stage are quite low, i.e., within 10% or less, and they increase with particle size. This observation suggests that particle losses are primarily caused by inertial deposition on the walls of the acceleration nozzles of the impactor as the flow turns, exiting a stage. For larger particles inertial effects are the most severe and hence higher losses are expected, which is in agreement with the experimental results.

One of the main concerns in conventional impactors is the possible degradation of the collection efficiency with particle loading. Previous investigations on the effect of loading on the impactor's performance characteristics showed that the collection efficiency of impactors using coated substrates degrades over time because the grease become ineffective with particle accumulation (Reischl and John, Staub-Reinhalt Luft., 38, 55, 1978; Turner and Hering, J. of Aerosol Sci., 18(2):215–224, 1987; and Tsai and Cheng, Aerosol Sci. and Technol., 23:96–106, 1995). Incoming particles bounce off those previously deposited. This degradation poses a serious limitation to sampling high concentrations aerosols or sampling over prolonged time periods, both of which would lead to high particle loading.

Experiments were conducted to identify a maximum particle mass loading range (in micrograms or milligrams of PM) in a given PCIS stage beyond which particle collection efficiency for any particle size would decrease due to particle bounce. These test were conducted for the 0.25 and 1.0 µm stages using PTFE substrates. The 0.25 µm stage was chosen for particles in the 0.1–0.5 µm range because the highest jet velocities of that stage would accentuate particle bounce. Evaluation of the degree to which particle bounce occurs for coarse (i.e., 2.5–10 µm) particle was conducted using the 1.0 µm stage. Although these particles are collected on the 2.5 µm stage, collection efficiency results with any of the substrates used, as discussed in the previous section, demonstrate that particle bounce is much less pronounced due to substantially lower jet velocity of this stage compared to the 1.0 μm cutpoint stage (Table 1, above). Hence, the 1.0 μm stage was chosen as it provides a worse case scenario for particle bounce of coarse PM collected by the PCIS.

The effect of particle loading on the performance of the 0.25 μm stage was investigated by generating polydisperse ammonium sulfate aerosol in a process similar to that used to characterize the impactor's collection efficiency. The volume median diameter of the generated aerosol, measured by means of the SMPS, was approximately 0.3–0.4 μm (GSD=1.8) SMPS measurements upstream and downstream of the impactor in the beginning of this experiment further confirmed that over 95% of the aerosol by mass is collected by the impactor. The stability of the concentration of the generated aerosol throughout the loading test was confirmed y means of the DataRAM, also sampling in parallel to the PCIS and SMPS samplers. Every 15 minutes, particle penetration though the PCIS 0.25 μm stage was determined for selected particle sizes viz., 0.1, 0.3 and 0.5 μm by adjusting manually the voltage of the SMPS and by measuring the concentrations for each size upstream and immediately downstream of the PCIS. Particle loading for the 1 μm stage was investigated by generating monodisperse PSL particles in a process similar to that used to characterize the impactor collection efficiency. Three particle sizes viz. 2.6, 5.4, and 7.6 μm were used. DataRAM was used to measure particle penetration through the PCIS 1.0 μm stage. Particle penetration was similarly determined every 15 minutes by measuring the concentration of particles upstream and downstream of the PCIS. At the end of each of these experiments, which lasted for about 1–2 hours, the Teflon filter used as an impaction substrate was weighed using a Mettler 5 Microbalance (MT 5, Mettler-Toledo Inc., Highstown, N.J.), under controlled relative humidity (e.g., 40%–45%) and temperature (e.g., 22–24° C.) conditions.

Figure 17:
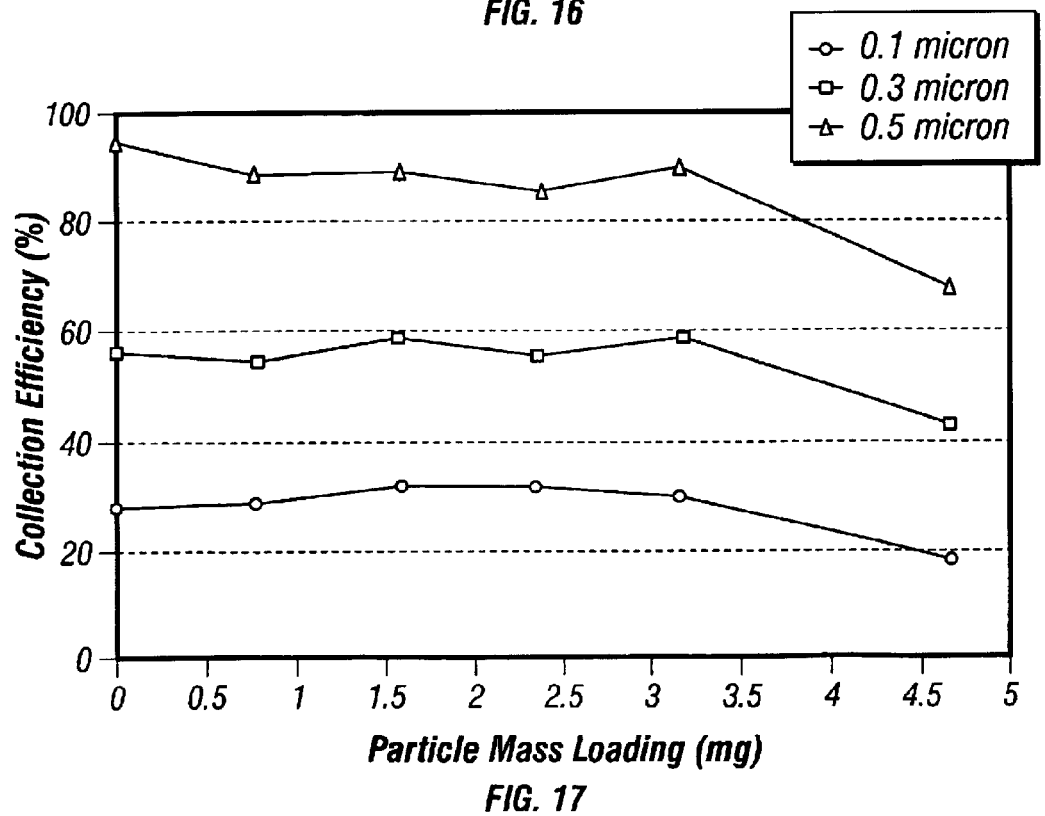

Results from the loading tests of 0.25 μm stage are shown in FIG. 17, in which the collection efficiency of the PCIS 0.25 μm stage for three different particle sizes viz., 0.1, 0.3, and 0.5 μm is plotted as a function of particle loading, expressed in mg of accumulated particles. The data plotted in FIG. 17 unequivocally demonstrate that particle bounce and reentrainment, which would have been manifested by a detectable decrease in the collection efficiency measured for any size, do not occur for loadings at least as high as 3.16 mg. It should be noted that this is an unrealistically high particulate loading for any stage of the PCIS, considering typical PM levels in ambient, indoor, or occupational environments. For example, for a 24 hours sampling period, and at a PCIS nominal flow rate of 9 LPM, this loading would correspond to an aerosol concentration of about 240 μg/m³ in each PCIS stage.

Figure 18:
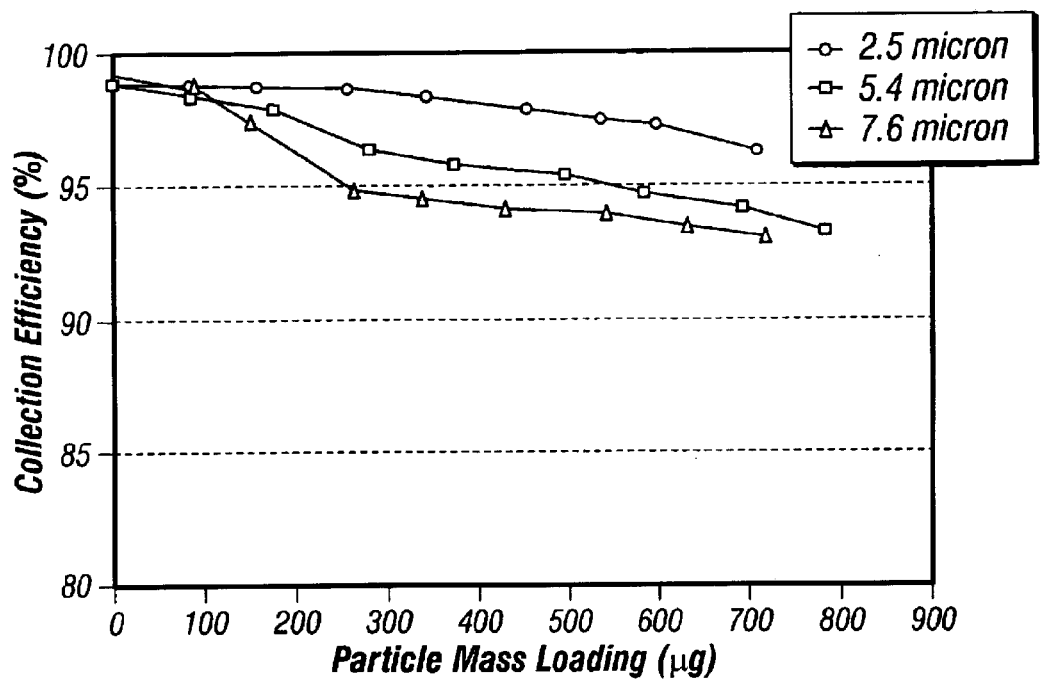

The collection efficiency of the PCIS 1.0 μm stage for three different particle sizes viz., 2.6, 5.4, and 7.6 μm is plotted in FIG. 18 as a function of particle loading, expressed in μg of accumulated particles. The plotted data reveal a slightly decreasing trend in the collection efficiency as particle loading increases, which is probably the result of particle bounce and reentrainment. This hypothesis is further corroborated by the faster decline in collection efficiency observed with increasing particle size. However, collection efficiencies of all three particle sizes tested remain well above 90% for mass loadings as high as 700 μg, a loading which, for a 24 hour sampling period, and at a sampling PCIS flow rate of 9 LPM, would correspond to an average aerosol concentration of about 54 μg/m³. These results therefore suggest that the PCIS retains its high collection efficiency for coarse PM even at these unusually high concentrations.

In addition to laboratory characterization using stable aerosols, test were performed to evaluate the performance of the PCIS using polydisperse ammonium nitrate aerosols generated also using the same process described herein. A solution of approximately 1 mg of nitrate per 1 ml of deionized water was used in the nebulizer to generate a targeted aerosol mass median diameter (MMD) of 0.3–0.4 μm. These test were conducted to provide an estimate of the degree to which labile constituents of ambient aerosols, such as ammonium nitrate, are preserved as they are drawn through the stages of the PCIS. First, the particle collection efficiency of the 0.25 and 0.50 μm stages for volatile ammonium nitrate aerosol was compared to those obtained using non-volatile ammonium sulfate aerosols. Subsequently, the nitrate PCIS concentrations (determined by adding the concentrations of all 5 stages) were compared with a collocated Micro-Orifice Uniform Deposit Impactor (MOUDI Model 110, MSP Corp., Minneapolis, Minn.) operating at a flow rate of 30 LPM. PTFE substrates were used both in PCIS as well as the MOUDI. In addition to the MOUDI, the size distribution of the generated ammonium nitrate aerosol was also measured using a SMPS, sampling in parallel to the PCIS and MOUDI. For the SMPS data, each particle size interval was converted from mobility equivalent diameter to aerodynamic diameter. This conversion was made using the following equation (Peters, Chein, and Lundgren, Aerosol Sci. Technol., 19:396–405, 1993):

$$\sqrt{C_a}\,d_a = \sqrt{\frac{C_{me}\rho_p}{\chi\rho_0}d_{me}} \quad (3)$$

where $d_a$ is aerodynamic diameter, $d_{me}$ is the mobility equivalent diameter, $C_a$ is the slip correction factor for the aerodynamic diameter, $C_{me}$ is the slip correction factor for the mobility equivalent diameter, $X$ is the dynamic shape factor, $\rho_p$ is the density of the particle, and $\rho_0$ is the unit density (1 g/cm³). When performing this conversion, the mobility equivalent diameter was assumed to be equal to the equivalent volume diameter (Kasper, 1982), while particles were assumed to be perfect spheres (dynamic shape factor, X=1). For each test, number concentrations for each size interval were then converted to mass concentrations using the following equation:

$$C_m = \frac{\pi}{6}\rho_p N_c \left(\frac{d_a}{\sqrt{\rho_p}}\right)^3 \quad (4)$$

where $C_m$ is mass concentration and $N_c$ is number concentration.

For each type of aerosol, particle mass concentrations obtained from the MOUDI were grouped in the following size ranges <0.18, 0.18–0.32, 0.32–0.5, 0.5–1.0 μm, whilst for PCIS, the ranges were: <0.25, 0.25–0.5, 0.5–1.0 μm. The MOUDI does not have a 0.25 μm cutpoint stage. In order to therefore make the MOUDI cutoff size ranges comparable to those of the PCIS, half of the nitrate mass determined in the 0.18–0.32 μm size range was added to that measured in the 0–0.18 μm range and half to that in the 0.32–0.5 μm range. This conversion was justified as follows: assuming that the generated nitrate particles are lognormally distributed (an assumption corroborate by the SMPS data obtained concurrently), about 50% of the particle mass in the 0.18–0.32 μm size range should be found above and below the geometric mean of that range, which is equal to 0.24 μm. The introduced uncertainty is minimal given the narrow width of the particle size range.

Figure 19:
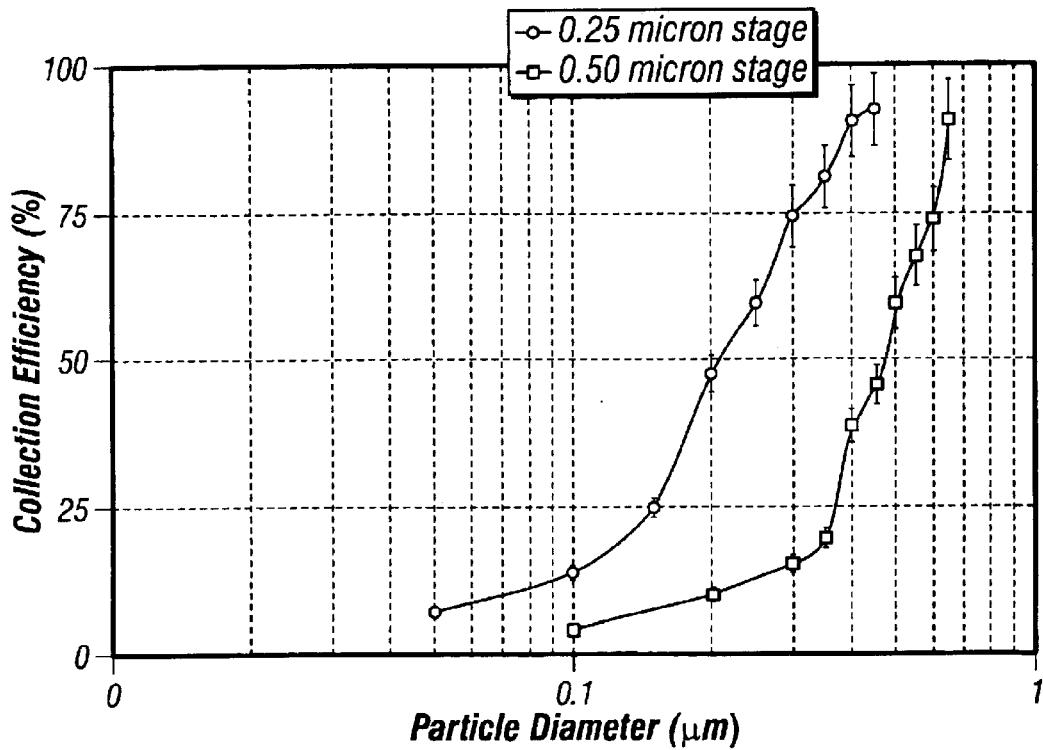

The evaluation of 0.25 μm and 0.5 μm stages using polydisperse ammonium nitrate aerosols is presented in FIG. 19. As evident, the cutpoints of the stages are conserved even when a labile aerosol is passed through the PCIS. There were no notable difference in the particle collection efficiency data obtained for stable sulfate and volatile nitrate aerosols. Previous studies have shown that losses of volatile compounds from the collected particulate matter are substantially reduced (if not eliminated) when these particles are collected by impaction compared to filtration (Wang and John, Aerosol Sci. and Technol., 8(2):157–172, 1988; Sioutas et al., Aerosol Sci. and Technol., 21:137–148, 1994). These studies showed that ambient ammonium nitrate concentrations obtained with impactors were 3–4 times higher than those obtained with standard Teflon filter samplers. This is an exceedingly important feature of impactors, particularly as a significant fraction of fine particles is associated with labile species such as ammonium nitrate and semi-volatile organic compounds.

The results from the laboratory evaluation of PCIS, MOUDI and SMPS using polydisperse ammonium nitrate aerosols are shown in Table 3, below. As evident from the data, a very good agreement persists between the concentrations of PCIS and SMPS for all three size ranges: 0.5–1.0, 0.25–0.5, and <0.25 μm. The total ammonium nitrate concentrations measured by PCIS and SMPS agree to within 10% or less. The concentrations for the MOUDI however, appear to be quite low for size ranges <0.25 μm in almost all the tests. This could well be attributed to the high flow rate of MOUDI (30 LPM) and consequently a relatively high pressure drop across its 0.18 μm stage as well as the after-filter, which would enhance volatilization of ammonium nitrate. The pressure drop across the 0.18 μm and after filter MOUDI stages are 24.4 and 50 inches of $H_2O$, respectively, compared to 3.9 and 4.7 inches of $H_2O$ of the last two PCIS stages. This difference in pressure drop apparently causes substantial volatilization of ammonium nitrate from the MOUDI filter. The ability of the PCIS to fractionate by size and collect particles under a low pressure drop, which in turn minimizes volatilization classes, is an exceedingly important feature, particularly because a significant fraction of fine particles is associated with labile species such as ammonium nitrate and semi-volatile organic compounds in large metropolitan areas like Los Angeles. Furthermore, personal activities including smoking and cooking are also known to generate particles with a large fraction of volatile constituents. The agreement between the SMPS and PCIS ammonium nitrate concentrations clearly supports the volatile species are preserved during particle collection by the PCIS.

TABLE 3

Comparison between concentrations of Ammonium Nitrate for PCIS, MOUDI and SMPS

| Particle size range (μm) | Concentration (μg/m³) | | |
|---|---|---|---|
| | PCIS | MOUDI | SMPS |
| TEST I | | | |
| 0.5–1.0 | 18.3 | 26.7 | 17.8 |
| 0.25–0.5 | 63.3 | 82.2 | 73.0 |
| <0.25 | 123.3 | 25.6 | 98.0 |
| Total | 204.0 | 144.5 | 188.8 |
| TEST II | | | |
| 0.5–1.0 | 22.1 | 38.9 | 15.8 |
| 0.25–0.5 | 40.0 | 58.9 | 52.6 |
| <0.25 | 83.3 | 13.3 | 74.4 |
| Total | 145.4 | 111.1 | 142.8 |
| TEST III | | | |
| 0.5–1.0 | 29.7 | 31.1 | 16.4 |
| 0.25–0.5 | 63.3 | 86.7 | 66.0 |
| <0.25 | 91.0 | 24.4 | 94.0 |
| Total | 184.0 | 142.2 | 178.4 |
| TEST IV | | | |
| 0.5–1.0 | 18.3 | 20.6 | 15.3 |
| 0.25–0.5 | 73.3 | 88.9 | 72.8 |
| <0.25 | 94.0 | 43.3 | 98.8 |
| Total | 185.6 | 152.8 | 186.9 |

The 2.5 cm Teflon filters are commercially available and chemically inert (thus ideal for most types of chemical analysis). Particles below 0.25 μm are collected on 3.7 cm Teflon filters of the same type with those as impaction substrates, in order to maintain consistency. The collection efficiency as a function of particle size for the 0.25, 0.50, 1.0, and 2.5 μm cutpoint stages were determined using polydisperse ammonium sulfate aerosols and PSL particles using various substrates, viz., PTFE, quartz and aluminum. No substantial difference between the coated quartz, and the uncoated PTFE and quartz impaction substrates were observed for the 0.25 μm stage. All three substrates have the same 50% collection efficiency cutpoint, approximately at 0.22–0.23 μm in aerodynamic diameter, thus very close to the design cutpoint.

For all four PCIS impactor stages, quartz substrates were associated with higher collection efficiencies and less sharp separation characteristics, both of which are attributed to capture of particles smaller than the cutpoint on the fibrous quartz surface because of partial entrainment of the impinging jet stream on that surface. Particle loading tests indicated that each PCIS stage could retain its collection efficiency for particle loadings up to 3.16 mg for fine PM and 700 μg for coarse PM.

Experimental tests using ammonium nitrate as the test aerosol indicated that the cutpoints of the 0.25 and 0.5 μm stages were conserved. Furthermore, the ammonium nitrate concentrations measured by the PCIS were in very good agreement with those measured by a collocated SMPS, whereas the concentrations of a collocated MOUDI were found to be lower to those of the SMPS and PCIS. The lower MOUDI concentration, observed particularly in the lower stage and the after-filter were attributed to volatilization of nitrate particles collected under low pressure in these stages: The ability of the PCIS to preserve labile species during sampling is a highly desirable feature, particularly as a significant fraction of fine particles is associated with such species.

A number of embodiments of the invention have been described. Nevertheless, it will be understood that various modifications may be made without departing from the spirit and scope of the invention. Accordingly, other embodiments are within the scope of the following claims.

What is claimed is:

1. A device comprising:
an inlet port at a first end;
a pump fluidly connected to the inlet port;
a plurality of orifice plates, each orifice plate comprising an orifice;
a plurality of impactor stage plates, each impactor stage plate comprising an impaction surface having a predetermined cutpoint for particulate matter, which allows characterizing particles from about 10 μm to less than 0.25 μm; and
a filter plate at a second end,
wherein the inlet port is fluidly connected to the filter plate such that a pressure drop from the first end to the second end is between about 8 and 15 inches of $H_2O$ with a flow rate of between 7 and 11 liters per minute (LPM), each orifice plate and impactor stage plate alternately disposed between the first end and second end, wherein each orifice plate is immediately followed by an impactor stage plate.

2. The device of claim 1, wherein the flow rate is about 8–10 LPM.

3. The device of claim 1, wherein the flow rate is about 9 LPM.

4. The device of claim 1, wherein the pressure drop is about 10–12 inches of $H_2O$.

5. The device of claim 4, wherein the pressure drop is about 11 inches of $H_2O$.

6. The device of claim 1, wherein the device comprises 4 impactor stages.

7. The device of claim 6, wherein the cutpoint of each impaction surface in each of the 4 impactor stages in order from the first end to the second end is about 2.5 to 10 μm, 1.0 to 2.5 μm, 0.5 to 1.0 μm, and 0.25 to 0.5 μm.

8. The device of claim 7, wherein the cutpoint of a first impaction surface in a first impactor stage closest to the inlet port is 2.5 μm.

9. The device of claim 8, wherein the cutpoint of a second impaction surface in a second impactor stage following the first impactor stage is 1.0 μm.

10. The device of claim 9, wherein the cutpoint of a third impaction surface in a third impactor stage following the second impactor stage is 0.5 μm.

11. The device of claim 10, wherein the cutpoint of a fourth impaction surface in a fourth impactor stage following the third impactor stage is 0.25 μm.

12. The device of claim 7, wherein the filter plate comprises a filter having a cutpoint of <0.25 μm.

13. A personal cascade impactor sampler (PCIS) system, comprising a miniaturized cascade impactor assembly (MCIA) comprising:
an inlet port at a first end;
a plurality of orifice plates, each orifice plate having an orifice;
a plurality of impactor stage plates, each impactor stage plate comprising an impaction surface having a predetermined cutpoint for particulate matter; and
a filter plate at a second end,
wherein the inlet port is fluidly connected to the filter plate such that a pressure drop from the first end to the second end is between about 8 and 15 inches of $H_2O$, each orifice plate and impactor stage plate alternately disposed between the first end and second end, wherein each orifice plate is immediately followed by an impactor stage plate;
a pump, fluidly connected to the MCIA such that the pump maintains a flow rate of between about 7 and 11 liters per minute (LPM); and
a power device in electrical communication with the pump.

14. The PCIS system of claim 13, wherein the flow rate is about 8–10 LPM.

15. The PCIS system claim 13, wherein the flow rate is about 9 LPM.

16. The PCIS system of claim 13, wherein the pressure drop is about 10–12 inches of $H_2O$.

17. The PCIS system of claim 16, wherein the pressure drop is about 11 inches of $H_2O$.

18. The PCIS system of claim 13, wherein the cutpoint of the impaction surfaces range from 10 μm to 0.1 μm.

19. The PCIS system of claim 13, wherein the device comprises 4 impactor stages.

20. The PCIS system of claim 19, wherein the cutpoint of each impaction surface in each of the 4 impactor stages in order from the first end to the second end is about 2.5 to 10 μm, 1.0 to 2.5 μm, 0.5 to 1.0 μm, and 0.25 to 0.5 μm.

21. The PCIS system of claim 20, wherein the cutpoint of a first impaction surface in a first impactor stage closest to the inlet port is 2.5 μm.

22. The PCIS system of claim 21, wherein the cutpoint of a second impaction surface in a second impactor stage following the first impactor stage is 1.0 μm.

23. The PCIS system of claim 22, wherein the cutpoint of a third impaction surface in a third impactor stage following the second impactor stage is 0.5 μm.

24. The PCIS system of claim 23, wherein the cutpoint of a fourth impaction surface in a fourth impactor stage following the third impactor stage is 0.25 μm.

25. The PCIS system of claim 20, wherein the filter plate comprises a filter having a cutpoint of <0.25 μm.

* * * * *